United States Patent
Rademaker et al.

(10) Patent No.: US 10,211,162 B2
(45) Date of Patent: Feb. 19, 2019

(54) METHOD FOR DETERMINING MISALIGNMENT BETWEEN A FIRST AND A SECOND ETCHING ZONES

(71) Applicant: COMMISSARIAT A L'ENERGIE ATOMIQUE ET AUX ENERGIES ALTERNATIVES, Paris (FR)

(72) Inventors: Guido Rademaker, Grenoble (FR);
Salim Boutami, Grenoble (FR);
Jonathan Pradelles, Saint-Martin-d'Uriage (FR)

(73) Assignee: Commissariat A L'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 15/879,577

(22) Filed: Jan. 25, 2018

(65) Prior Publication Data

US 2018/0233456 A1   Aug. 16, 2018

(30) Foreign Application Priority Data

Jan. 30, 2017   (FR) ..................................... 17 50759

(51) Int. Cl.
*H01L 21/00*   (2006.01)
*H01L 23/544*   (2006.01)
(Continued)

(52) U.S. Cl.
CPC .......... *H01L 23/544* (2013.01); *G01B 11/272* (2013.01); *G03F 1/78* (2013.01);
(Continued)

(58) Field of Classification Search
CPC . H01L 23/544; H01L 21/68; H01L 21/67259; H01J 37/3174
See application file for complete search history.

(56) References Cited

U.S. PATENT DOCUMENTS 7,666,559 B2 *   2/2010  Schulz ................ G03F 7/70633
                                                        257/48
7,876,439 B2 *   1/2011  Ausschnitt .......... G03F 7/70633
                                                        257/797
(Continued)

FOREIGN PATENT DOCUMENTS

EP   1 628 164 B1        10/2010
EP     3355118 A1 *       8/2018    ............... G03F 1/78
(Continued)

OTHER PUBLICATIONS

French Preliminary Search Report and Written Opinion dated Nov. 16, 2017 in Patent Application No. 1750759 (with English language translation of categories of cited documents).
(Continued)

*Primary Examiner* — Laura Menz
(74) *Attorney, Agent, or Firm* — Oblon, McClelland, Maier & Neustadt, L.L.P.

(57) ABSTRACT

This method for measuring the misalignment between a first and a second etching zone includes: producing a plasmonic antenna including a first and a second element that are separate and each delineate a cavity on one respective side, all of the elements of the plasmonic antenna that are situated on a first side of a separating plane being produced entirely inside the first zone and all of the elements of the plasmonic antenna that are situated on the second side of the separating plane being produced entirely inside the second zone, and after the production of the plasmonic antenna, the method includes: measuring the absorption rate of the plasmonic antenna, and determining the magnitude of the misalignment between the first and second zones on the basis of the measured absorption rate and of a predicted value for this absorption rate in the absence of a misalignment.

14 Claims, 3 Drawing Sheets

(51) Int. Cl.
| | |
|---|---|
| *G03F 1/78* | (2012.01) |
| *G03F 1/84* | (2012.01) |
| *G03F 7/20* | (2006.01) |
| *G01B 11/27* | (2006.01) |
| *H01J 37/317* | (2006.01) |
| *H01L 21/67* | (2006.01) |
| *H01L 21/68* | (2006.01) |
| *H01L 21/66* | (2006.01) |
| *G01N 21/552* | (2014.01) |

(52) U.S. Cl.
CPC ............ *G03F 1/84* (2013.01); *G03F 7/70633* (2013.01); *G03F 7/70683* (2013.01); *H01J 37/3174* (2013.01); *H01L 21/67259* (2013.01); *H01L 21/68* (2013.01); *H01L 22/10* (2013.01); *G01N 21/554* (2013.01); *H01J 2237/31798* (2013.01); *H01L 2223/5442* (2013.01); *H01L 2223/54426* (2013.01)

(56) References Cited

U.S. PATENT DOCUMENTS

| | | | | |
|---|---|---|---|---|
| 8,339,605 | B2* | 12/2012 | Ausschnitt | G03F 7/70633 257/797 |
| 8,345,243 | B2* | 1/2013 | Ghinovker | G03F 7/70633 257/797 |
| 8,666,532 | B2* | 3/2014 | Amit | H05K 3/4679 700/109 |
| 8,755,647 | B2* | 6/2014 | Yaacobi | G02B 6/264 385/27 |
| 8,767,183 | B2* | 7/2014 | Den Boef | G03F 7/70633 355/55 |
| 9,613,972 | B1* | 4/2017 | Kim | H01L 21/764 |
| 9,927,718 | B2* | 3/2018 | Kandel | G03F 7/70683 |
| 10,018,751 | B2* | 7/2018 | Verschuuren | H01L 33/507 |
| 2007/0008533 | A1* | 1/2007 | Ghinovker | G03F 7/70633 356/401 |
| 2011/0229010 | A1 | 9/2011 | Arnz et al. | |
| 2012/0044470 | A1 | 2/2012 | Smilde et al. | |
| 2013/0148194 | A1* | 6/2013 | Altug | G01N 21/554 359/350 |
| 2014/0132948 | A1 | 5/2014 | Shchegrov | |
| 2014/0211195 | A1 | 7/2014 | Barcelo et al. | |
| 2015/0198524 | A1 | 7/2015 | Sapiens et al. | |
| 2017/0336198 | A1* | 11/2017 | Adel | G01B 11/272 |
| 2018/0233456 | A1* | 8/2018 | Rademaker | G03F 1/78 |

FOREIGN PATENT DOCUMENTS

| | | | | |
|---|---|---|---|---|
| FR | | 3062516 A1 * | 8/2018 | ............... G03F 1/78 |
| WO | WO 2016/086056 A1 | | 6/2016 | |

OTHER PUBLICATIONS

Tine Greibe, et al., "Quality control of JEOL JBX-9500FSZ e-beam lithography system in a multi-user laboratory", Microelectronic Engineering, vol. 155, XP029562503, 2016, pp. 25-28.

Alexei Smolyaninov, et al., "Meta-Coaxial Nanoantenna", 2014 Conference on Lasers and Electro-optics (CLEO)—Laser Science to Photonic Applications, XP032707605, Jun. 2014, 2 pages.

William Arnold, et al., "Manufacturing Challenges in Double Patterning Lithography", Semiconductor Manufacturing, 2006, pp. 283-286.

Shakeeb Bin Hasan, et al., "Nonlinear plasmonic antennas", Materials Today, vol. 17, No. 10, Dec. 2014, pp. 478-485.

Hsu-Ting Huang, et al., "Spectroscopic ellipsometry and reflectometry from gratings (Scatterometry) for critical dimension measurement and in situ, real-time process monitoring", Thin Solid Films, 2004, 9 pages.

K. Schraml, et al., "Optical proportics end interparticle coupling of plasmonic bowtie nanoantennas on a semiconducting substrate", Physical Review B, vol. 90, 2014, 7 pages.

P. Biagioni, et al., "Cross Resonant Optical Antenna", Physical Review Letters, vol. 102, Jun. 2009, pp. 1-4 and cover page.

Alexei Smolyaninov, et al., "Broadband metacoaxial nanoantenna for metasurface and sensing applications", Optics Express, vol. 22, No. 19, Sep. 2014, 8 pages.

Holger Fischer, et al., "Engineering the optical response of plasmonic nanoantennas", Optic Express, vol. 16, No. 12, Jun. 2008, pp. 9144-9154.

Sylvain Vedraine, et al., "On the absorption and electromagnetic field spectral shifts in plasmonic nanotriangle arrays", Optic Express, vol. 22, No. 11, May 2014, pp. 13308-13313.

* cited by examiner

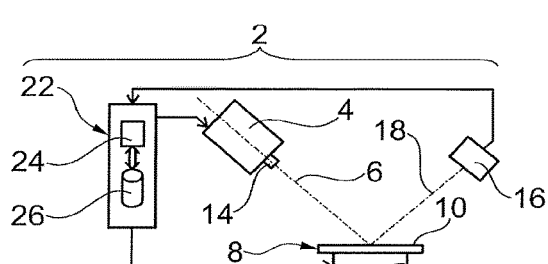
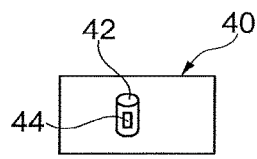
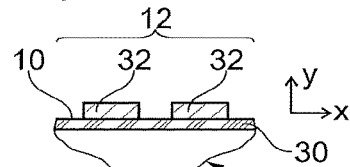
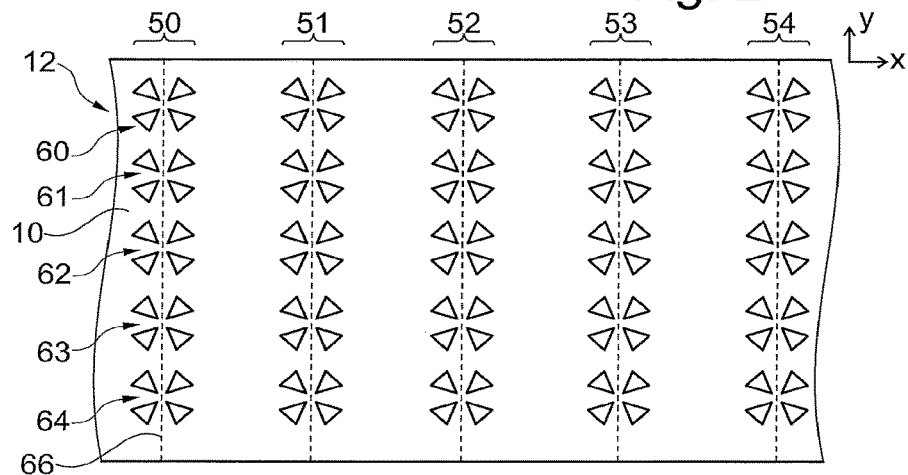
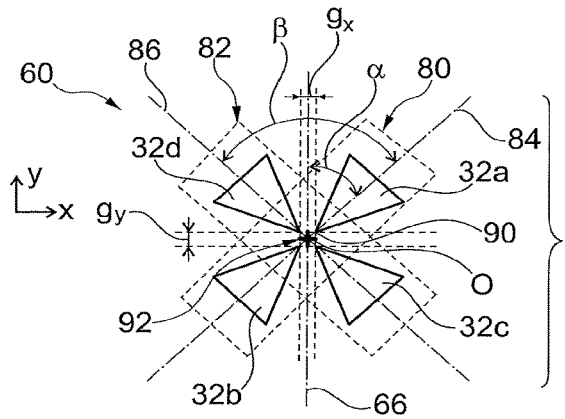
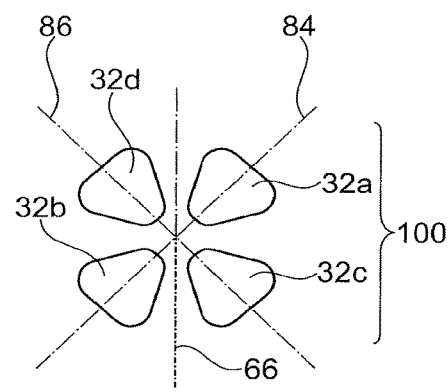

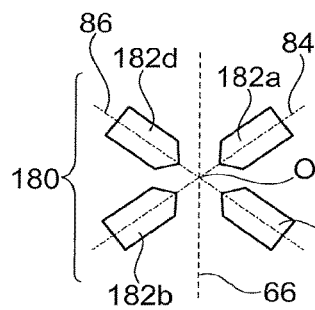
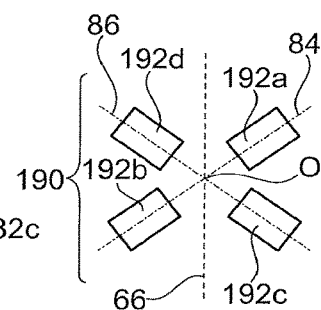
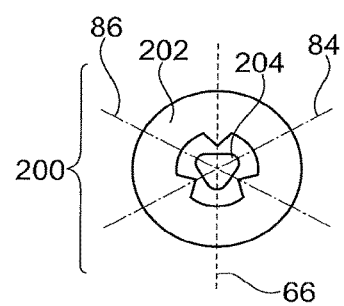
Fig. 15  Fig. 16  Fig. 17
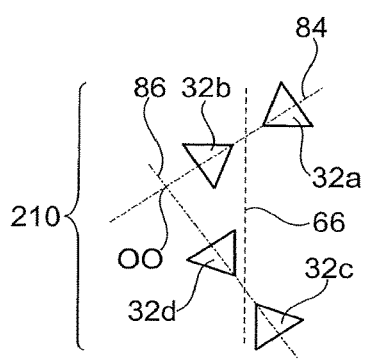
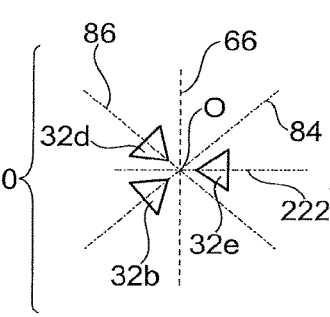
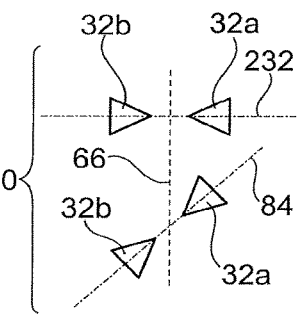
Fig. 18  Fig. 19  Fig. 20
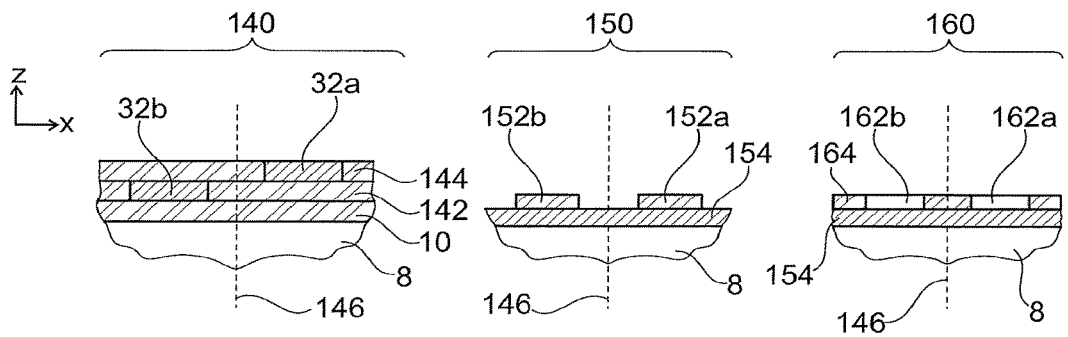
Fig. 12  Fig. 13  Fig. 14

METHOD FOR DETERMINING MISALIGNMENT BETWEEN A FIRST AND A SECOND ETCHING ZONES

The invention relates to a method for measuring the misalignment between a first and a second etching zone. Other subjects of the invention are an information recording medium, a measuring apparatus and a blueprint for a reference pattern for implementing this misalignment measurement method.

An etching zone is a zone of a substrate inside which an element or a portion of an element is etched. This substrate is known under the term 'wafer'. The first and second etching zones are such that there may be an unintentional misalignment between these two etching zones, that is to say an unwanted offset of one etching zone with respect to the other. An offset is 'unwanted' or 'unintentional' when this offset does not exist in the blueprint encoding the dimensions, the layout and the position of the elements to be etched on the substrate, but exists once these elements have actually been produced on the substrate. This offset is caused by faults or calibration errors in the machines used to produce these elements on the substrate. Among the various machines that are used to produce these elements on the substrate, it is often the lithography machine that is the root cause of the greatest offsets.

A lithography machine is for example an electron beam lithography machine.

An electron beam lithography machine is often used to write patterns in a layer of resin deposited on the face of the substrate. The layer of resin is sensitive to the electrons of the beam. Next, for example, regions of the resin that have not been irradiated by the electron beam are eliminated, and a mask that conceals certain regions of the face of the substrate is thus obtained, and other regions are left directly exposed to the outside. Then, by applying an etching agent through this mask, the regions that are not concealed by the mask are eliminated, whereas the regions that are concealed by this mask are protected and are therefore not etched. Such a mask therefore makes it possible to etch the patterns written in the face of the substrate.

Using a single-beam electron beam lithography machine, without moving the substrate with respect to the source of this electron beam, it is possible to write a pattern in only a small etching zone. To this end, the electron beam is moved by deflection, while keeping the source of this beam stationary with respect to the substrate. This small zone is called a 'field' or 'exposure field' in the case of an electron beam lithography machine. The surface area of this field is often smaller than or equal to 1 cm$^2$ or 1 mm$^2$. It is therefore far smaller than the surface area of the face of the substrate to be etched. As a result, to write over the entire face of the substrate, it is necessary to move the substrate and the source of the electron beam with respect to one another. In this case, the substrate and the source occupy various relative positions with respect to one another over time. Each relative position of the substrate with respect to the source of the electron beam corresponds to a respective field. The various fields that are used to write over the entire face of the substrate are generally aligned in lines and in columns that are contiguous or overlap one another slightly. However, due to inaccuracies regarding the position of the substrate with respect to the electron beam, a case may arise whereby two contiguous fields are not perfectly aligned with respect to one another. There is then a misalignment between these two fields. Such a misalignment is also known under the term 'stitching' or 'field stitching'. Such a misalignment may cause an abrupt breakage or an unwanted deformation of a pattern straddling these two fields.

It is therefore desirable to measure this misalignment, that is to say to measure the magnitude thereof, so as to correct it and limit the magnitude thereof.

To this end, known methods for measuring the misalignment include:
providing a blueprint containing instructions encoding in particular the dimensions, the layout and the position of a reference pattern to be produced, on a substrate, straddling the first and second zones,
producing the reference pattern on the substrate by executing the instructions contained in the provided blueprint and by using a lithography machine, and then
determining the magnitude of the misalignment on the basis of the observation of the reference pattern produced on the substrate.

For example, the following article describes the production, on the substrate, of a reference pattern in the form of a Vernier scale, and the measurement of the misalignment using a scanning electron microscope: Tine Greibe et al: '*Quality control of JEOL JBX-9500FSZ e-beam lithography system in a multi-user laboratory*', Microelectronic Engineering 155 (2016) 25-28.

Such a misalignment measurement method is slow and complicated, as it is necessary to use a scanning electron microscope.

The same problem exists with multi-beam electron beam lithography machines. These multi-beam machines, unlike a single-beam machine, make it possible to simultaneously irradiate a plurality of fields that are adjacent to one another each with its own electron beam. These adjacent fields are aligned next to one another. However, as in the case of a single-beam machine, there may be a misalignment between these various adjacent fields that are irradiated simultaneously. In the case of multi-beam machines, at least one of the dimensions of the fields is generally much smaller than the dimensions of the fields of a single-beam machine. For example, this smaller dimension may be smaller than 10 μm or 2 μm.

In the latter case, there is an additional problem, namely that the known reference patterns are too large to be produced inside a single field of a multi-beam machine.

When various structured layers are superimposed above one another, there may also be a misalignment between these various layers. A structured layer is a layer that has been etched so as to produce one or more elements there. In this case, each structured layer corresponds to a respective etching zone, and this misalignment is sometimes referred to using the expression 'overlay accuracy'. This is measured similarly to what has just been described in the particular case of the misalignment between two fields of an electron beam lithography machine. It will be noted that the misalignment between two layers may exist regardless of the technology that is used by the lithography machine to write the patterns to be etched. For example, the problem of the misalignment between two structured layers is also encountered when a photolithography machine has been used to write the elements to be etched.

There are thus many situations in which the misalignment between two etching zones has to be measured.

The prior art also discloses:
US2011/229010A1,
US2015/198524A1,
US2014/132948A1,
US2014/211195A1.

The invention aims to provide a simple and quick method for measuring the misalignment between two etching zones. One subject thereof is therefore such a method in accordance with claim 1.

In the method that is claimed, if there is a misalignment between the first and the second etching zones, then this alters the dimensions of the cavity of the plasmonic antenna, and therefore the absorption rate of this plasmonic antenna. Thus, on the basis of the measured absorption rate of the plasmonic antenna and of a predicted value for this absorption rate in the absence of a misalignment, it is possible to determine the magnitude of the misalignment between these two etching zones. The absorption rate of the plasmonic antenna is able to be measured easily and quickly using a source of polarized radiation and a sensor for sensing the intensity of the reflected radiation. As a result, the method that is claimed makes it possible to quickly and simply measure the misalignment between two etching zones without having to use complex and slow hardware, such as a scanning electron microscope, to achieve this.

In addition, the dimensions of a plasmonic antenna may be smaller than 10 μm or 5 μm. The method that is claimed may thus be implemented to measure a misalignment between etching zones that are much smaller than what is possible with conventional reference patterns.

Lastly, if the zones are fields of an electron beam lithography machine, in order to produce the plasmonic antenna, it is not necessary for these fields to overlap one another. By contrast, to produce conventional reference patterns, it is often necessary to provide such an overlap between the two adjacent fields.

The embodiments of this measurement method may include one or more of the features of the dependent method claims.

Another subject of the invention is an information recording medium including instructions for implementing the method that is claimed when these instructions are executed by a microprocessor.

Another subject of the invention is an apparatus for measuring the misalignment between a first and a second etching zone for implementing the method that is claimed.

Another subject of the invention is a blueprint for a reference pattern for implementing the method that is claimed.

The invention will be better understood upon reading the following description, given solely by way of nonlimiting example and made with reference to the drawings, in which:

FIG. 1 is a schematic illustration of an apparatus for measuring the misalignment between two etching zones;

FIG. 2 is a schematic and partial illustration, in vertical section, of a portion of a substrate used to measure a misalignment between two etching zones;

FIG. 3 is a schematic illustration of an electron beam lithography machine;

FIG. 4 is a schematic and partial illustration, seen from above, of a reference pattern used to measure a misalignment between two etching zones;

FIG. 5 is a more detailed illustration of a plasmonic antenna from the reference pattern of FIG. 4;

FIG. 6 is a schematic illustration of a reference pattern effectively produced on a substrate on the basis of a blueprint encoding the reference pattern of FIG. 5;

FIGS. 12 to 14 are schematic, partial illustrations, in vertical section, of other possible embodiments of the reference pattern of FIG. 4;

FIGS. 15 to 20 are schematic illustrations, seen from above, of various other possible embodiments for a plasmonic antenna from the reference pattern of FIG. 4.

In these figures, the same references are used to denote the same elements. Hereinafter in this description, the features and functions that are well known to those skilled in the art are not described in detail.

FIG. 1 shows an apparatus 2 for measuring a misalignment between two etching zones. Hereinafter, the description is given in the particular case in which these etching zones correspond to adjacent fields of a multi-beam electron beam lithography machine 40 (FIG. 3).

Figure 7:
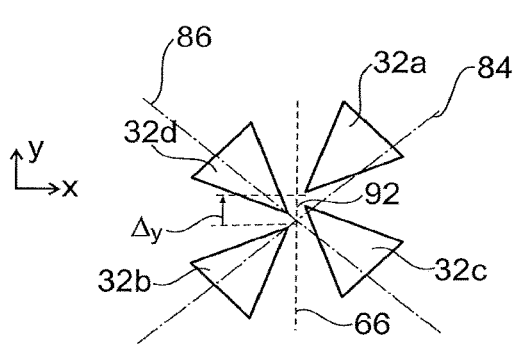
FIGS. 7 to 10 are schematic illustrations, seen from above, of various misalignments liable to be encountered when producing the reference pattern of FIG. 4 on a substrate.

The apparatus 2 includes a radiation source 4 that is capable of emitting a polarized beam 6 at a wavelength $\lambda_m$ in the direction of a substrate 8 on the upper face 10 of which a reference pattern 12 has been produced (FIG. 2). For example, the beam 6 is a beam that is collimated so as to irradiate only a chosen portion of the reference pattern 12.

The beam 6 is an electromagnetic wave. In this case, to boost the resolution of the apparatus 2, the wavelength $\lambda_m$ is less than 2000 nm or 700 nm and, generally, greater than 390 nm. The wavelength $\lambda_m$ is preferably between 390 nm and 700 nm, that is to say contained within the visible spectrum. In this case, the intensity of the beam 6 may be expressed in candela. If the wavelength $\lambda_m$ is outside of the visible spectrum, the intensity corresponds to the radiated power, that is to say to the energy flow.

The source 4 includes a rotating polarizer 14 that makes it possible to vary the direction of polarization of the beam 6 in response to a command.

The apparatus 2 also comprises:
- a sensor 16 capable of measuring the intensity of the radiation 18 reflected by a portion of the reference pattern 12,
- an actuator 20 capable of moving the substrate 8 with respect to the incident beam 6 so as to select the portion of the reference pattern 12 exposed to the beam 6, and
- a processing unit 22 capable of determining the magnitude of the misalignment between two etching zones on the basis of the measurements from the sensor 16 and of the intensity of the beam 6.

For example, the sensor 16 includes one or more photodetectors for this purpose.

The unit 22 is connected:
- to the sensor 16 so as to receive the intensity measurements, and
- to the source 4 and to the actuator 20 so as to control them.

For example, the unit 22 includes a programmable microprocessor 24 and a memory 26. The memory 26 includes in particular the instructions and the data that are necessary to execute the method of FIG. 11. In this example, the memory 26 also includes one or more conversion tables that make it possible to convert differences $E_x$ and $E_y$ into magnitudes expressed in meters or in subunits of meters.

FIG. 2 shows a portion of the substrate 8 in vertical section. In this description, the figures are oriented with respect to an orthogonal reference frame XYZ in which Z is the vertical direction and X and Y are two orthogonal horizontal directions. The upper face 10 of the substrate 8 is formed by a layer 30 made of dielectric material, on which layer elements 32 made of electrically conductive material are directly deposited. The combination of this layer 30 and the elements 32 forms the reference pattern 12. In this case, conductive material means a material whose electrical conductivity at 20° C. is greater than $10^5$ S/m and preferably greater than $10^6$ S/m. This typically involves a metal such as gold or silver. In this case, dielectric material means a material whose electrical conductivity at 20° C. is less than $10^{-2}$ S/m or less than $10^{-4}$ S/m. In this case, the elements 32 are made of gold and the layer 30 is a layer of silica.

FIG. 3 shows a multi-beam electron beam lithography machine 40 used to write, in a layer of resin that is sensitive to the electron beam, the patterns of the reference pattern 12 that define the dimensions, the layout and the position of the various elements 32 of this reference pattern. For example, this layer of resin is deposited on a metal layer that is itself directly deposited on the layer 30 made of dielectric material. This machine 40 includes a plurality of fields that are contiguous with one another and that extend parallel to the direction Y. The machine 40 also includes a memory 42 containing a blueprint 44. The blueprint 44 includes instructions that define the dimensions, the layout and the position of the various elements 32 of the reference pattern 12 on the substrate 8. Thus, when these instructions are executed by the machine 40, said machine writes, in the layer of resin, patterns that make it possible to obtain a mask. This mask is then used to etch the metal layer and thus produce the elements 32 of the reference pattern 12.

FIG. 4 shows, in more detail, the layout and the position of the reference pattern 12 as encoded in the blueprint 44. In this figure, the wavy lines on the right and on the left indicate that only a portion of the reference pattern 12 is shown. The reference pattern 12 includes a plurality of rows 50 to 54 that are parallel to the direction Y. These rows 50 to 54 are identical to one another, and only the row 50 is described in more detail.

The row 50 includes a plurality of plasmonic antennae 60 to 64 that are each arranged on either side of one and the same vertical separating plane. This vertical separating plane cuts the horizontal plane of the substrate at a separating line 66 that is parallel to the direction Y. The plane of the substrate is the plane in which the substrate 8 mainly extends. The line 66 is situated on the border between two adjacent fields 68 and 70 of the machine 40. Thus, one portion of the elements of each antenna 60 to 64 is situated inside the field 68, and the other portion of these elements is situated inside the field 70. The antennae 60 to 64 are identical to one another in this case, and only the antenna 60 is described in more detail.

FIG. 5 shows the antenna 60 as encoded by the instructions contained in the blueprint 44. The antenna 60 includes two pairs 80 and 82 of elements 32. In this case, the pairs 80 and 82 are situated in one and the same horizontal plane. The pair 82 is inferred from the pair 80 by a rotation of an angle β about a vertical axis passing through a point O situated on the line 66. In this case, the angle β is equal to 90°. As a result, only the pair 80 is now described in more detail.

To distinguish between the two elements 32 of the pair 80, in this figure and those that follow, they bear the numerical references 32a and 32b, respectively. Likewise, in this figure and those that follow, the two elements 32 of the pair 82 bear the numerical references 32c and 32d, respectively.

The elements 32a and 32b are situated to the right and to the left of the line 66, respectively. They are aligned with an oblique axis 84 that cuts the line 66 at the point O at an angle α. In this embodiment, the axis 84 is also an axis of symmetry for the elements 32a and 32b. The angle α is strictly greater than 0° and large enough that the element 32a is situated entirely on the right-hand side of the line 66 and does not touch this line 66. The angle α is also strictly less than 90°, such that the element 32a does not touch the element 32c. The angle α is typically between 25° and 65° or between 35° and 55°. In this case, the angle α is equal to 45° to within ±5° or to within ±2°.

The elements 32c and 32d, for their part, are aligned with an axis 86. The angle between the axes 84 and 86 is equal to the angle β. In this embodiment, the element 32b is additionally symmetrical with the element 32a about a horizontal axis perpendicular to the axis 84 and passing through the point O. In this case, this axis of symmetry is coincident with the axis 86. As a result, hereinafter, only the element 32a is described in more detail.

The element 32a includes a tip 90 directed toward the point O and separated from this point O by a distance g/2. There is therefore a distance g separating the tip 90 from the opposite tip of the element 32b. As a result of this distance g, there is a cavity 92 between these two tips. The same distance g exists between the opposing tips of the elements 32c and 32d. This distance g therefore sets the dimensions of the cavity 92 between the elements 32a, 32b and between the elements 32c, 32d. Only the horizontal dimension $g_X$ and the vertical dimension $g_Y$ of the cavity 92 have been shown in FIG. 5. These dimensions $g_X$, $g_Y$ are derived from the distance g using the following relationships: $g_X = g \cdot \cos(\alpha)$ and $g_Y = g \cdot \sin(\alpha)$, where the symbol '·' denotes the multiplication operation. In this example, the horizontal section of the element 32a is a solid triangle, and the tip 90 is one of the apexes of this triangle. In these conditions, the pairs 80 and 82 each form a first and a second plasmonic antenna, respectively, known under the term 'bowtie' antenna. For example, the triangle is an equilateral triangle.

It is recalled at this juncture that a 'bowtie' antenna produces surface plasmon resonance located inside the cavity 92 when said antenna is exposed to polarized incident radiation in a direction parallel to the plane of the substrate 8. In addition, typically, the pulse w of the incident radiation must be lower than the pulse $\omega_p$ of the electrically conductive material of the antenna, said pulse being defined by the following relationship: $\omega_p = (N \cdot e^2 / (\varepsilon_0 \cdot m^*))^{0.5}$, where:

N is the concentration of free charge carriers in the electrically conductive material, e is the charge of an electron, $\varepsilon_0$ is the vacuum permittivity, and m* is the effective mass of the free electrons in the electrically conductive material. In order for surface plasmon resonance to occur, it is generally also necessary for the real part of the relative permittivity of the electrically conductive material to be negative.

Hereinafter, $\lambda_{max}$ is used to denote that wavelength of the incident radiation at which the magnitude of the surface plasmon resonance is at a maximum. The value of this wavelength $\lambda_{max}$ depends on the dimensions of the element 32a.

Those skilled in the art know how to construct and dimension a 'bowtie' antenna such that a surface plasmon resonance is produced at a desired wavelength $\lambda_m$. In this case, the antenna 60 is dimensioned such that the wavelengths $\lambda_{max}$ and $\lambda_m$ are equal, to within ±10% or to within ±5%. For example, the dimensioning of the element 32a may be determined by FDTD ('finite-difference time domain') numerical simulation. Specifically, the principle and the laws of operation of the pair 80 are known and have already been simulated. On this subject, the reader may refer to the following studies, for example:

Sylvain Vedraine, Renjie Hou, Peter R. Norton, and François Lagugné-Labarthet, 'On the absorption and electromagnetic field spectral shifts in plasmonic nanotriangle arrays', Opt. Exp. 22, 13308 (2014).

K. Schraml, M. Spiegl, M. Kammerlocher, G. Bracher, J. Bartl, T. Campbell, J. J. Finley, and M. Kaniber, 'Optical properties and interparticle coupling of plasmonic bowtie nanoantennas on a semiconducting substrate', PRB 90, 035435 (2014).

In this case, the angle of incidence of the beam 6 at the wavelength $\lambda_m$ is strictly less than 90°. It is additionally chosen such that the majority of the beam 6 is reflected by the antenna 60. Due to the phenomenon of surface plasmon resonance, a portion of the intensity of the beam 6 is absorbed by the antenna 60. The absorption rate of a plasmonic antenna may be measured on the basis of the reflection rate and/or of the transmission rate of the radiation 6. The reflection rate is equal to the ratio $I_r/I_i$ and the transmission rate is equal to the ratio $I_t/I_i$, where:

$I_r$ is the intensity of the radiation reflected by the plasmonic antenna, $I_t$ is the intensity of the radiation transmitted through the plasmonic antenna, and $I_i$ is the intensity of the incident beam 6.

Hereinafter, in this embodiment, the absorption rate of the plasmonic antenna is measured by the reflection rate of the antenna 60.

The absorption rate varies depending on the dimensions $g_X$ and $g_Y$ of the cavity 92. By contrast, the value of the wavelength $\lambda_{max}$ is practically independent of these dimensions $g_X$ and $g_Y$.

FIG. 6 schematically shows a plasmonic antenna 100 formed on the substrate 8 by implementing the instructions encoding the antenna 60 and contained in the blueprint 44. The antenna 100 is shown in the particular case in which there is no misalignment between the fields 68 and 70. In FIG. 6, the elements of the antenna 100 corresponding to the elements of the antenna 60 bear the same numerical references. As illustrated in this figure, in practice, using current lithography techniques, it is not possible to produce perfect tips, such as those shown in FIG. 5. By contrast, when the antenna 60 is produced on the substrate 8, the tips, such as the tip 90, are replaced with rounded sections, such as illustrated in FIG. 6.

These deformations, introduced by the various steps of producing the antenna 60, may lead to the value of the wavelength $\lambda_{max}$ being altered. However, numerical simulations carried out showed that the wavelength $\lambda_m$ stayed sufficiently close to the wavelength $\lambda_{max}$ for the produced antenna 100 still to produce surface plasmon resonance inside the cavity 92 when said antenna is exposed to the radiation of wavelength $\lambda_m$. Thus, in spite of the differences between the theoretical form of the antenna 60 encoded in the blueprint 44 and the form actually obtained, the misalignment measurement method described hereinafter works. As a result, hereinafter in this description, as in the following figures, the differences between the dimensions of the antennae 60 and 100 are ignored so as to simplify the explanations. In particular, in the following figures, the elements 32a to 32d of the antenna 100 are shown as being identical to the elements 32a to 32d of the antenna 60.

FIGS. 7 to 10 show the antenna 100 when the misalignment between the fields 68 and 70 is non-zero. More precisely, Δx and Δy are used to denote the magnitude of the misalignment between the fields 68 and 70 parallel to the directions X and Y, respectively. By convention, the magnitudes Δx and Δy have a positive value if the misalignment corresponds to a movement of the elements 32a, 32c with respect to the elements 32b and 32d in the direction of the directions X and Y, respectively. By contrast, the magnitudes Δx and Δy have a negative value in the presence of a movement in the direction opposite to the directions X and Y.

Figure 8:
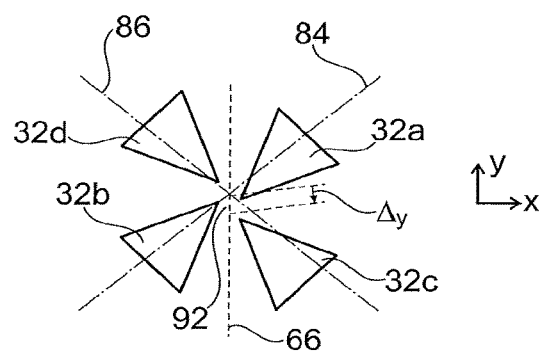
Figure 9:
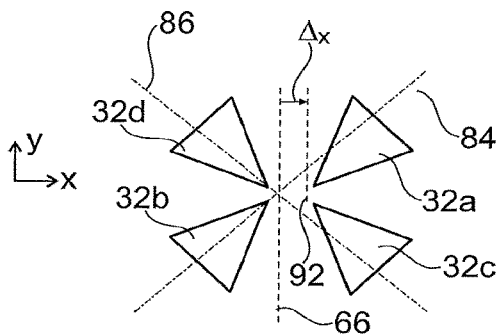
Figure 10:
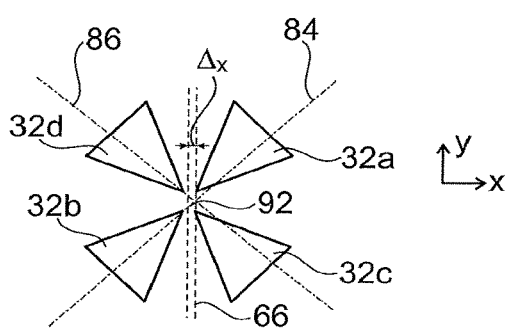

FIGS. 7 and 8 show the consequences of a misalignment when the magnitude Δx is zero and the magnitude Δy is positive (FIG. 7) or negative (FIG. 8). FIGS. 9 and 10 show the consequences of a misalignment when the magnitude Δy is zero and the magnitude Δx is positive (FIG. 9) or negative (FIG. 10).

As illustrated in these FIGS. 7 to 10, a non-zero misalignment between the fields 68 and 70 is manifested in an alteration of the dimensions of the cavity 92, and therefore in an alteration of the absorption rate at the wavelength $\lambda_m$. By contrast, a non-zero misalignment does not, or practically does not, alter the value of the wavelength $\lambda_{max}$, as the dimensions of the elements 32a to 32d are not altered. As a result, the absorption rate of the antenna 100 essentially varies depending on the misalignment between the fields 68 and 70. The magnitude of the misalignment is hence able to be determined on the basis of:

a predicted value of the absorption rate of the antenna 100 in the absence of a misalignment, that is to say for a misalignment of zero magnitude, and the absorption rate actually measured for the antenna 100.

In this particular embodiment, it is sought to measure the magnitude Δy and, at the same time, the magnitude Δx. In addition, in this embodiment, it is moreover desired to know the direction of movement of the elements 32a, 32c with respect to the elements 32b and 32d. To this end, it has been observed that, when the magnitude Δy of the misalignment is positive, the size of the cavity 92 between the elements 32a and 32b increases while the size of the cavity 92 between the elements 32c and 32d decreases. In these conditions, when the magnitude Δy increases, the absorption rate of the pair 80 decreases while, at the same time, the absorption rate of the pair 82 increases. The opposite behavior is observed when the magnitude Δy is negative. To make use of this property, a ratio $A_Y$ is defined by the following relationship: $A_Y = T_{+45}/T_{-45}$, where:

$T_{+45}$ is the absorption rate of the antenna 100 measured using incident radiation at the wavelength $\lambda_m$ and whose direction of polarization is parallel to the axis 86, and $T_{-45}$ is the absorption rate of the antenna 100 measured using incident radiation at the wavelength $\lambda_m$ and whose direction of polarization is parallel to the axis 84.

In addition, this ratio $A_Y$ has the advantage of depending very little on the magnitude of the misalignment Δx. Specifically, a non-zero magnitude Δx substantially alters the absorption rates $T_{-45}$ and $T_{+45}$ in the same way, such that the ratio $A_Y$ varies little in response to an alteration of the magnitude Δx. Lastly, when the magnitude Δy is zero, the dimensions of the cavity 92 between the elements 32a, 32b and between the elements 32c, 32d are identical, such that the absorption rates $T_{-45}$ and $T_{+45}$ are equal. Thus, the predicted value $A_{YP}$ of the ratio $A_Y$ is easy to predict, since it is equal to 1.

The difference $E_Y = 1 - A_Y$ hence varies mainly depending on the magnitude Δy, and much less so depending on the magnitude Δx. This difference $E_Y$ is therefore mainly representative of the magnitude of the misalignment between the fields 68 and 70 in the sole direction Y.

If necessary, this difference $E_Y$ may be converted into a value of the magnitude Δy expressed in nanometers using a conversion table. For example, this conversion table is constructed by calculating, through numerical simulation or through experimental measurements, the value of the difference $E_Y$ for various known values of the magnitude Δy. In this case, for the sake of simplicity, as a first approximation, it is considered that the difference $E_Y$ is equal, to within a multiplicative constant, to the magnitude Δy. In other words, the conversion table in this case gives the following relationship: Δy=A·$E_Y$, where A is a known multiplicative constant, determined during an initial calibration of the method.

The rates $T_{+45}$ and $T_{-45}$ of the antenna 100 may be measured by exposing this antenna 100 to polarized radiation in the directions parallel to the axes 86 and 84, respectively. Specifically, polarized radiation parallel to the axis 84 excites almost only the pair of elements 32a, 32b, and virtually does not excite the pair of elements 32c, 32d that are aligned with an axis orthogonal to the axis 84. The surface plasmon resonance inside the cavity 92 is hence due mainly to the elements 32a and 32b. The measured absorption rate with such polarized radiation hence corresponds to the absorption rate $T_{-45}$. Likewise, by exposing the antenna 100 to polarized radiation parallel to the direction 86, it is possible to measure the rate $T_{+45}$.

When the magnitude Δx is greater than 0 (FIG. 9), then the elements 32 that are closest to one another are the elements 32a and 32c and the elements 32b, 32d. In this case, by successively exposing the antenna 100 to radiations whose directions of polarization are parallel to directions Y and X, respectively, it may be observed that the absorption rate is higher with the radiation polarized in the direction Y than with the radiation polarized in the direction X. Specifically, the distance separating the element 32a from the elements 32d and 32b is greater than that separating this element 32a from the element 32c. By contrast, when the magnitude Δx is less than 0 (FIG. 10), it is the absorption rate measured with the radiation polarized in the direction Y that is lower than the absorption rate measured with the radiation polarized in the direction X. Specifically, in the latter case, the element 32a is closer to the element 32d than to the elements 32b and 32c.

To make use of this property, a ratio $A_X$ is defined as follows: $A_X=T_{90}/T_0$, where:

$T_{90}$ is the absorption rate of the antenna 100 measured using incident radiation at the wavelength $\lambda_m$ and whose direction of polarization is parallel to the direction X, and $T_0$ is the absorption rate of the antenna 100 measured using incident radiation at the wavelength $\lambda_m$ and whose direction of polarization is parallel to the direction Y.

This ratio $A_X$ varies depending on the magnitude Δx of the misalignment in the direction X. It has additionally been observed through numerical simulation that the ratio $A_X$ is practically independent of the magnitude Δy.

In the absence of a misalignment, that is to say for zero magnitudes Δx and Δy, the element 32a is at the same distance from the elements 32c and 32d. Thus, in the absence of a misalignment, the absorption rates $T_{90}$ and $T_0$ are equal and the predicted value $A_{XP}$ of the ratio $A_X$ is therefore equal to 1. As a result, the difference $E_X=1-A_X$ essentially varies depending on the magnitude Δx and practically not depending on the magnitude Δy. This difference $E_X$ is therefore representative of the magnitude of the misalignment in the sole direction X.

As for the transmission rates $T_{-45}$ and $T_{+45}$, the absorption rates $T_{90}$ and $T_0$ may be measured by exposing the antenna 100 to radiations whose directions of polarization are parallel to the directions Y and X, respectively.

Figure 11:
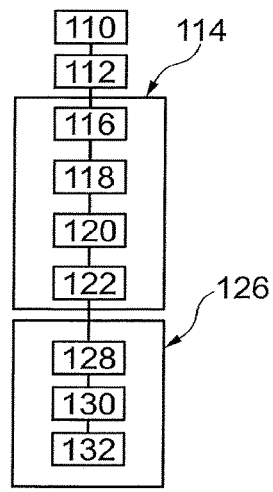
FIG. 11 is a flow chart of a method for measuring the misalignment between two etching zones using the reference pattern of FIG. 4 and the apparatus of FIG. 1.

FIG. 11 shows a method for measuring the misalignment between the fields 68 and 70 using the apparatus 2 and the reference pattern 12.

During a step 110, the blueprint 44 for the reference pattern 12 is initially designed and then provided to the machine 40. It is typically recorded in the memory 42.

Next, during a step 112, the reference pattern 12 is produced on the substrate 8, using the machine 40 to achieve this. Typically, during this step, the machine 40 exposes a layer of resin, directly deposited on a metal layer, to the electron beam of this machine 40. During this step, the electron beams write the reference pattern 12 into this layer of resin that is sensitive to the electron beams. Next, the portions of this non-exposed layer of resin are eliminated so as to form an etching mask. The metal layer is then etched through this mask so as to form, in this metal layer, the elements 32 of the reference pattern 12. The reference pattern 12 and in particular the antenna 100 are thus obtained.

During this step 112, the elements 32a, 32c are produced inside the field 70, whereas the elements 32b, 32d are produced inside the field 68. Thus, if there is a misalignment between these fields 68 and 70, this is manifested inevitably in an offset of the elements 32a, 32c with respect to the elements 32b and 32d, and therefore in an alteration of the dimensions $g_X$ and $g_Y$ of the cavity 92.

Once the reference pattern 12 has been produced on the substrate 8, during a step 114, the absorption rates $T_{+45}$, $T_{-45}$, $T_{90}$ and $T_0$ are measured using the apparatus 2. During this step, the beam 6 is for example directed over a single plasmonic antenna or over a restricted group of plasmonic antennae of the reference pattern 12. For example, the restricted group contains only a plurality of plasmonic antennae straddling one and the same border between two contiguous fields. Such a restricted group may contain between two and ten plasmonic antennae. In this case, the remainder of this description is given in the particular case in which the beam 6 is directed over the single antenna 100. However, everything that is described in this particular case also applies to the case of the other plasmonic antennae of the reference pattern 12 and to the case of a restricted group of plasmonic antennae.

To direct the beam 6 over the antenna 100, the actuator 20 is controlled by the unit 22 so as to move the substrate 8 with respect to the beam 6.

Once the beam 6 has been directed over the antenna 100, the unit 22 carries out an operation 116 of measuring the absorption rate $T_{-45}$. To this end, the unit 22 controls the polarizer 14 so as to select a direction of polarization parallel to the axis 84. Next, the unit 22 controls the source 4 so as to expose the antenna 100 to the beam 6 that is thus polarized. The intensity $I_i$ of the beam 6 is known. In parallel, the sensor 16 measures the intensity $I_r$ of the radiation reflected by the antenna 100 and transmits this measurement to the unit 22, which acquires said measurement. In response, the unit 22 calculates the absorption rate $T_{-45}$.

Step 114 also includes operations 118, 120 and 122 that are identical to operation 116, except that, during some of these operations, the unit 22 controls the polarizer 14 so as to have directions of polarization that are parallel to the axis 86, to the direction Y and then to the direction X, respectively. Thus, at the end of operations 116, 118, 120 and 122, the unit 22 has measured the absorption rates $T_{-45}$, $T_{45}$, $T_{90}$ and $T_0$.

Step 114 is repeated for each plasmonic antenna of the reference pattern 12 or for each restricted group of plasmonic antennae of the reference pattern 12. In addition, in this particular example, step 114 is reiterated for various wavelengths $\lambda_{mi}$, where the index i is an identifier of the wavelength used to carry out the measurements of the absorption rates $T_{45}$, $T_{-45}$, $T_{90}$ and $T_0$. This step 114 is typically repeated for at least two and preferably at least five or ten different wavelengths $\lambda_{mi}$. For example, these wavelengths $\lambda_{mi}$ are distributed uniformly over an interval centered around the predicted value for the wavelength $\lambda_{max}$.

Once the desired absorption rates have been measured, during a step 126, the unit 22 determines various production errors introduced by the machine 40.

More precisely, during an operation 128, the unit 22 determines the magnitude Δy of the misalignment in the direction Y. To this end, the unit 22 calculates the difference $E_Y$ and then converts this difference into an amplitude Δy expressed in nanometers using the conversion table. In addition, the sign of this difference $E_Y$ gives the direction of the movement, parallel to the direction Y, of the elements 32a, 32c with respect to the elements 32b, 32d.

During an operation 130, the unit 22 determines the magnitude Δx of the misalignment in the direction X. Operation 130 is identical to operation 128, except that the difference $E_X$ is used instead of the difference $E_Y$. Thus, at the end of these operations 128 and 130, the unit 22 has determined the magnitude and the direction of the misalignment parallel to the directions X and Y of the fields 68 and 70.

In addition to the misalignment between the fields 68, 70, there may also be errors that alter the dimensions of the elements 32. A dimensioning error is typically caused by an error with the focusing of the electron beam in the layer of resin. For example, if the focal point of the electron beam is situated below the layer of resin, then the dimensions of the elements 32a to 32d are enlarged. Such a dimensioning error may be expressed in the form of a scale factor expressed as a percentage with respect to the dimensions encoded in the blueprint 44.

In this case, to quantify the dimensioning error, during an operation 132, the unit 22 estimates the value of the wavelength $\lambda_{max}$. To this end, the unit 22 uses the absorption rates calculated at the various wavelengths $\lambda_{mi}$. Specifically, when the magnitude of the surface plasmon resonance is at a maximum, this also corresponds to a maximum of the absorption rate. To estimate this value of the wavelength $\lambda_{max}$, the unit 22 is able to use only the absorption rates measured with just one or, by contrast, with a plurality of directions of polarization. Next, still during this operation 132, the unit 22 calculates a difference $E_D$ between the estimated value of the wavelength $\lambda_{max}$ and a predicted value for this wavelength $\lambda_{max}$ in the absence of a misalignment. Specifically, an alteration of the dimensions of the cavity 92 virtually does not alter the value of the wavelength $\lambda_{max}$. The predicted value of the wavelength $\lambda_{max}$ is for example predicted through numerical simulation or measured experimentally in the absence of a misalignment. Next, the difference $E_D$ thus calculated is converted into a percentage or into a magnitude expressed in nanometers using a conversion table.

Steps 128, 130 and 132 may be reiterated for other plasmonic antennae situated on the same separating line 66. In this case, the magnitudes Δx and Δy are typically equal to an average of the magnitudes Δx and Δy that are obtained from each plasmonic antenna situated on the line 66.

It has been observed that the ratios $A_X$ and $A_Y$ vary by practically 10% for a magnitude Δx or Δy of a few nanometers. Thus, by applying the method described here, it is possible to measure a misalignment with a resolution of less than 1 nm or 2 nm.

FIG. 12 shows another embodiment of the reference pattern 12 in which the antenna 100 is replaced with a plasmonic antenna 140. The antenna 140 is identical to the antenna 100, except that the elements 32b and 32d are arranged inside a layer 142 made of dielectric material, which layer is deposited directly on the layer 10. The elements 32a and 32c are deposited inside a layer 144 made of dielectric material, which layer is deposited directly on the layer 142. In FIG. 12, only the elements 32a and 32b have been shown. In this embodiment, the layers 142 and 144 correspond to two separate etching zones, since they are etched one after the other using one and the same lithography machine, for example. More precisely, the lithography machine is used once to construct the etching mask of the layer 142, and then a second time to construct the etching mask of the layer 144. In this embodiment, the lithography machine may be the machine 40 or another lithography machine, such as a photolithography machine. Similarly to what was described in the case of the misalignment between the fields 68, 70, there may be a misalignment in the direction X and/or in the direction Y between the layers 142 and 144. This misalignment may be measured in the directions X and Y by using the plasmonic antenna 140 instead of the antenna 100 and, for example, by implementing the same method as the one described with reference to FIG. 11.

In FIG. 12 and in FIGS. 13 and 14, a vertical separating plane 146 has been shown. This plane 146 corresponds to the separating plane described previously. In particular, everything that has been described in the case of the line 66 applies to the orthogonal projections of the elements 32 in the plane of the substrate. Specifically, the orthogonal projection of the plane 146 in the plane of the substrate forms the separating line between the orthogonal projections of the elements 32.

FIG. 13 shows a plasmonic antenna 150 that is capable of replacing the antenna 100 for measuring the misalignment between the fields 68 and 70 in the directions X and Y. The antenna 150 is identical to the antenna 100, except that:
  the elements 32a to 32d are replaced with elements 152a to 152d, respectively, and
  the layer 30 is replaced with a layer 154 made of electrically conductive material.

In FIG. 13, only the elements 152a and 152b have been shown. In this embodiment, the elements 152a to 152d are identical to the elements 32a to 32d, respectively, except that they are made of dielectric material. The elements 152a to 152d are typically made of a resin that is sensitive to the electron beam. Thus, this embodiment avoids a step of etching a layer made of electrically conductive material in order to produce a plasmonic antenna. However, owing to its construction, the variation in the absorption rate of the antenna 150 depending on its dimensions $g_X$ and $g_Y$ is not as quick as in the case of the antenna 100, such that the resolution of the measurement method is lower with the antenna 150.

FIG. 14 shows a plasmonic antenna 160 capable of replacing the antenna 150. The antenna 160 is identical to the antenna 150, except that the elements 152a to 152d are replaced with elements 162a to 162d, respectively. In FIG. 14, only the elements 162a and 162b are shown. The form of the elements 162a to 162d is identical to that of the elements 152a to 152d, except that these elements 162a to 162d are cavities formed in a layer 164 made of dielectric material that is deposited directly on the layer 154. This embodiment has the same advantages and drawbacks as that of FIG. 13.

Many other embodiments of a plasmonic antenna including at least two separate elements and liable to be used to implement the method of FIG. 11 are possible. For example, the elements 32a to 32d may be replaced with elements of a different form, such as those shown in FIGS. 15 to 17.

FIG. 15 shows a plasmonic antenna 180 identical to the antenna 60, except that the elements 32a to 32d are replaced with elements 182a to 182d, respectively. In this embodiment, each element 182a to 182d is formed by the juxtaposition of a triangle and a rectangle or a square. One side of the rectangle forms one side of the triangle. Such an embodiment of a plasmonic antenna 180 is described for example in more detail in the following article: P. Biagoni et al: 'Cross Resonant Optical Antenna', Physical Review Letter, no. 102, 256801, Jun. 26, 2009.

FIG. 16 shows a plasmonic antenna 190 identical to the antenna 60, except that the elements 32a to 32d are replaced with elements 192a to 192d, respectively. The elements 192a to 192d are identical to the elements 32a to 32d, except that a rectangle or a square, and no longer a triangle, are involved.

FIG. 17 shows a plasmonic antenna 200 including two concentric elements 202 and 204. Such a plasmonic antenna is described in more detail in the following article: Alexei Smolyaninov et al: '*Broadband metacoaxial nanoantenna for metasurface and sensing applications*', Optics Express 22786, Vol. 22, No. 19, Sep. 22, 2014. This embodiment is particularly suitable for the case in which the etching zones between which it is necessary to measure a misalignment are different layers, such as the layers 142 and 144 of FIG. 12. In this case, for example, the element 202 is produced inside the layer 142 and the element 204 is produced inside the layer 144. In this particular embodiment, the separating plane between the elements 202 and 204 is horizontal and parallel to the plane of the substrate.

Other embodiments of a plasmonic antenna may also be obtained by arranging the elements 32a to 32d differently with respect to one another. By way of illustration, FIGS. 18 to 20 show three different plasmonic antennae each liable to be used instead of the antenna 60.

FIG. 18 shows a plasmonic antenna 210 identical to the antenna 60, except that the axes 84 and 86 intersect at a point OO remote from the line 66.

FIG. 19 shows a plasmonic antenna 220 identical to the antenna 60, except that the elements 32a and 32c are replaced with a single element 32e of identical form to the element 32a. The element 32e is aligned with an axis 222 perpendicular to the line 66 and passing through the point O.

FIG. 20 shows a plasmonic antenna 230 identical to the antenna 210, except that the axis 84 is replaced with an axis 232 perpendicular to the line 66.

The method for measuring a misalignment using plasmonic antennae, such as those shown in FIGS. 15 to 20, is inferred from the explanations given in the case of the method of FIG. 11.

Variants of the Reference Pattern 12:

The number of plasmonic antennae contained in the reference pattern 12 may be different. In a simplified case, the reference pattern 12 includes a single plasmonic antenna or a single plasmonic antenna per separating border between two etching zones.

The reference pattern 12 may include a plurality of plasmonic antennae that are different from one another. For example, these various plasmonic antennae differ from one another by way of their dimensions.

Variants of the Plasmonic Antenna:

Other metals may be used as electrically conductive material to produce the plasmonic antenna, such as for example copper, aluminum or cobalt. Metal alloys may also be used, such as for example AuK. Metal nitrides may also be used, such as for example TiN, ZrN, HfN and tertiary forms thereof, such as TiZrN, etc.

The electrically conductive material used to produce the plasmonic antennae is not necessarily a metal. For example, it may involve a transparent conductive oxide, such as for example indium-tin (ITO) or GZO ('gallium-doped zinc oxide') or AZO ('aluminum-doped zinc oxide'), etc.

The conductive material may also be a highly doped semiconductor material, or even a two-dimensional material, such as graphene or $MoF_2$ ('Molybdenum disulfide').

The angle β may be other than 90°. For example, the angle β is between 60° and 85°.

The substrate 8 may be made of metal. In this case, the layer 10 is made of silica, and its thickness is for example equal to $\lambda_m/2$ or $\lambda_m/4$.

Other embodiments of the plasmonic antenna are still possible. For example, the elements 32 may be formed inside the dielectric layer and be exposed flush on the face 10. In this case, the elements 32 may be manufactured using a damascene or BEOL ('back end of line') method. The elements 32 may also be formed on the end of respective pillars made of dielectric material. Typically, in the latter case, the pillars are formed in the layer made of dielectric material. The element 32 generally then covers the horizontal end of the pillar and at least some of the vertical walls of the pillar.

Variants of the Misalignment Measurement Method:

In some particular cases, for technical reasons, the magnitude Δx or the magnitude Δy is systematically equal to 0. In these cases, only the difference $E_X$ or the difference $E_Y$ is measured. In addition, if the misalignment is able to exist in only one direction, the plasmonic antenna may also be simplified. For example, if only the magnitude Δx is able to adopt a value other than 0, then the elements 32c and 32d are omitted, and the elements 32a and 32b are aligned with an axis perpendicular to the line 66. If, by contrast, the magnitude Δx is systematically equal to 0, then the pair 80 or the pair 82 may be omitted.

When the substrate 8 and the layer 10 are transparent to the polarized incident radiation, it is possible to measure the absorption rate on the basis of the transmission rate of the incident radiation through the plasmonic antenna instead of, or in addition to, using the reflection rate. To measure the transmission rate of the plasmonic antenna, the sensor 16 has to be positioned on the side of the substrate 8 opposite the side exposed directly to the beam 6.

As a variant, the beam 6 illuminates the entire surface of the substrate 8 or a region of the substrate 8 containing plasmonic antennae straddling various separating lines. The misalignment is measured as described previously. However, in this case, the measured misalignment is an average of the existing misalignments between the various fields illuminated by the beam 6.

In one simplified embodiment, the direction of misalignment is not determined.

If it is not necessary to determine the magnitude of the misalignment in two precise orthogonal directions, and it is desired simply to obtain a value representative of the magnitude of the misalignment without it being necessary to know the direction in which this misalignment occurs, then the measured absorption rates $T_{45}$, $T_{-45}$, $T_{90}$ and $T_0$ may be combined differently. In particular, it is not necessary to calculate the ratios $A_X$ and $A_Y$ described previously. For example, it is possible to determine the magnitude of the misalignment in terms of absolute value from the relationship $(T_{45}^2 + T_{-45}^2)^{0.5}$ or $(T_{90}^2 + T_0^2)^{0.5}$. In these last two cases, the method may be simplified either by omitting the measurements of the absorption rates $T_{90}$ and $T_0$ or by omitting the measurement of the absorption rates $T_{45}$ and $T_{-45}$.

The conversion of the difference $E_X$ and/or $E_Y$ into nanometers may be omitted. For example, such a conversion is unnecessary for comparing the measurements with one another.

If necessary, it is possible to correct the measurement of the magnitude $\Delta y$ using the measured magnitude $\Delta x$. Specifically, the simulations carried out show that the measurement of the magnitude $\Delta x$ is more decorrelated from the magnitude $\Delta y$ than the other way round.

As a variant, the measurement of a dimensioning error is omitted. In this case, it is not necessary to reiterate step 114 for various wavelengths $\lambda_{mi}$, and operation 132 is omitted.

Other embodiments for measuring a dimensioning error are possible. For example, the absorption rate of the antenna is measured at a wavelength $\lambda_0$ at which the surface plasmon resonance of the plasmons located inside the cavity 92 does not occur. The absorption rate of the antenna measured at the wavelength $\lambda_0$ is denoted '$T_{\lambda 0}$'. To this end, the wavelength $\lambda_0$ is chosen to be remote from the wavelength $\lambda_{max}$. For example, the difference between the wavelengths $\lambda_0$ and $\lambda_{max}$ is greater than 100 nm or 150 nm or 200 nm. The rate $T_{\lambda 0}$ is not sensitive to misalignment errors. By contrast, this rate $T_{\lambda 0}$ is sensitive to dimensioning errors of one or more of the elements 32. In particular, a dimensioning error that impacts only some of the elements 32 of the antenna 60 is manifested in a difference between the rate $T_{\lambda 0}$ and a normal absorption rate $T_{\lambda 0ref}$. The rate $T_{\lambda 0ref}$ is the absorption rate at the wavelength $\lambda_0$ of the antenna in the absence of a dimensioning error. This rate $T_{\lambda 0ref}$ may be determined by numerical simulations or measured experimentally. By contrast, in the absence of a dimensioning error, the rates $T_{\lambda 0}$ and $T_{\lambda 0ref}$ are identically sensitive. A dimensioning error is hence detected if the difference between the rates $T_{\lambda 0}$ and $T_{\lambda 0ref}$ is greater than a predetermined threshold. If the difference between these rates $T_{\lambda 0}$ and $T_{\lambda 0ref}$ is smaller than this predetermined threshold, no dimensioning error is detected. If a dimensioning error is detected, measurement of the misalignment using this antenna may be prohibited, for example.

That which has just been described in the previous paragraph may be performed for a plurality of separate wavelengths $\lambda_{0i}$ at which surface plasmon resonance of the plasmons located inside the cavity 92 does not occur. These wavelengths $\lambda_{0i}$ may be chosen to be greater or less than the wavelength $\lambda_{max}$.

The spectrum of the reflection or transmission rate of the antenna 92 may be measured over a range of wavelengths containing not only the wavelengths $\lambda_m$ and $\lambda_{max}$ but also the wavelength $\lambda_0$ or the wavelengths $\lambda_{0i}$. To this end, for example, the radiation 6 is polychromatic radiation. In this case, the same measured spectrum may be used to determine both a dimensioning error and a misalignment error.

The measurement of a dimensioning error may be implemented independently of the misalignment measurement. In this case, the method of FIG. 11 is simplified. In particular, steps 116, 118 or 120, 122 may be omitted, and steps 128 and 130 are omitted. If only a dimensioning error is measured, the antenna 60 does not have to straddle a separating border between two different etching zones. For example, the antenna 60 may in this case be situated right in the middle of a field.

Main Advantages of the Described Embodiments:

The difference $E_Y$ varies mainly depending on the magnitude of the misalignment in a direction parallel to the line 66. As a result, this difference makes it possible to measure the magnitude $\Delta y$ of the misalignment in a single precise direction, regardless of the magnitude $\Delta x$.

When the plasmonic antenna encoded in the blueprint 44 includes elements 32c and 32d that are inferred, by rotation, from the elements 32a and 32b, the predicted value $A_{YP}$ of the ratio $A_y$ is simple to calculate and to predict.

Measuring absorption rates for incident radiations whose directions of polarization are parallel to the directions X and Y, respectively, additionally makes it possible to measure the magnitude $\Delta x$.

When the orthogonal projection, in the plane of the substrate, of the plasmonic antenna encoded by the blueprint 44 is symmetrical about the line 66 and about a horizontal axis perpendicular to this line 66, and if the axis 84 additionally cuts the line 66 at an incline of 45°, then the determination of the magnitude of the misalignment is simplified, as the predicted values $A_{YP}$ and $A_{XP}$ of the ratios $A_y$ and $A_x$ are simple to predict.

The fact that the elements 32a to 32d are triangles makes it possible to obtain a plasmonic antenna for which the wavelength $\lambda_{max}$ virtually does not vary depending on the dimensions of the cavity 92. Thus, when measuring the absorption rate, it is not necessary to vary the wavelength $\lambda_m$ of the incident radiation depending on the estimated magnitude of the misalignment. In addition, these triangle-shaped elements form bowtie antennae. It is possible with such antennae to achieve a resolution of one nanometer for the misalignment measurement. Specifically, an alteration of a few nanometers brings about a significant alteration of the absorption rate. In this text, a significant alteration of the absorption rate is an increase or a decrease in the absorption rate of greater than or equal to $0.01 \cdot Ap$ and preferably greater than or equal to $0.05 \cdot Ap$ or $0.1 \cdot Ap$ in response to a one-nanometer variation in the dimension $g_x$ or $g_y$ with respect to the same dimension encoded in the blueprint 44, where Ap is the predicted value of the absorption rate in the absence of a misalignment.

The use of elements 32 made of conductive material makes it possible to obtain significant variations in the absorption rate, and therefore a very good resolution.

When the elements 32 are made of dielectric material or are cavities hollowed out of a dielectric material, the measurement method is simpler to implement, as the steps of etching a layer made of conductive material are omitted.

Measuring the absorption rate at a wavelength $\lambda_m$ of less than 2000 nm or 700 nm makes it possible to achieve a resolution of less than or equal to 2 nm or 1 nm.

The invention claimed is:

1. A method for measuring the misalignment between a first and a second etching zone, an etching zone being a zone of a substrate inside which an element or a portion of an element is etched, this method including:
   providing a blueprint containing instructions encoding in particular the dimensions, the layout and the position of a reference pattern to be produced, on a substrate, straddling the first and second zones, producing the reference pattern on the substrate by executing the instructions contained in the provided blueprint and by using a lithography machine, and then determining the magnitude of the misalignment on the basis of the observation of the reference pattern produced on the substrate, wherein:

the reference pattern encoded by the instructions contained in the blueprint includes at least one plasmonic antenna capable, after having been produced on the substrate, of producing surface plasmon resonance located inside a cavity when said antenna is exposed to polarized incident radiation of wavelength $\lambda_m$ such that the plasmonic antenna absorbs at least a portion of the polarized incident radiation at this wavelength $\lambda_m$, the absorption rate of this plasmonic antenna at the wavelength $\lambda_m$ varying depending on a dimension of the cavity, this plasmonic antenna including, to this end, a first and a second element that are separate and each delineate the cavity on one respective side such that the dimension of the cavity is set by the spacing between these first and second elements, these first and second elements each being situated entirely on a first and on a second respective side of a separating plane, respectively, when the reference pattern is produced, all of the elements of the plasmonic antenna that are situated on the first side of the separating plane are produced entirely inside the first zone and all of the elements of the plasmonic antenna that are situated on the second side of the separating plane are produced entirely inside the second zone, after the production of the plasmonic antenna, the method includes:

measuring the absorption rate of the produced plasmonic antenna at the wavelength $\lambda_m$ by exposing this plasmonic antenna to incident polarized radiation of wavelength $\lambda_m$ and known intensity, emitted by a radiation source, and by measuring the intensity of the radiation reflected by the plasmonic antenna or transmitted through the plasmonic antenna at this same wavelength $\lambda_m$ using a radiation intensity sensor; and determining the magnitude of the misalignment between the first and second zones on the basis of the measured absorption rate and of a predicted value for this absorption rate in the absence of a misalignment between the first and second zones.

2. The method as claimed in claim 1, wherein the instructions contained in the provided blueprint encode a plasmonic antenna in which:

the first and second elements are aligned with a first axis of alignment such that the absorption rate of the produced plasmonic antenna reaches a first maximum when it is exposed to a first incident radiation of wavelength $\lambda_m$ and with a direction of polarization parallel to this first axis of alignment, and the plasmonic antenna includes third and fourth elements that are separate and bound, each on one respective side, the same cavity or another cavity, these third and fourth elements being situated entirely inside the first and second sides, respectively, and these third and fourth elements being aligned with a second axis of alignment that cuts the first axis of alignment at a point of intersection, such that the absorption rate of the plasmonic antenna reaches a second maximum when it is exposed to a second incident radiation of wavelength $\lambda_m$ and with a direction of polarization parallel to this second axis of alignment, the measurement of the absorption rate includes:

a first measurement of an absorption rate Tm1 of the plasmonic antenna when it is exposed to the first incident radiation, and a second measurement of an absorption rate Tm2 of the plasmonic antenna when it is exposed to the second incident radiation, the determination of the magnitude of the misalignment includes determining the magnitude of the misalignment between the first and second zones, in a direction parallel to a separating line, this separating line being formed by the intersection of the separating plane and the plane of the substrate, depending on the difference between the ratio Tm1/Tm2 and a ratio Tp1/Tp2, where Tp1 and Tp2 are the predicted values of the absorption rate, in the absence of a misalignment, for the first and second measurements, respectively.

3. The method as claimed in claim 2, wherein, in the provided blueprint, the orthogonal projection, in the plane of the substrate, of the pair formed by the third and fourth elements is inferred from the orthogonal projection, in this same plane, of the pair formed by the first and second elements, by:

a rotation whose center is situated on the separating line, in combination with a translation parallel to this separating line, the magnitude of this translation being greater than or equal to zero.

4. The method as claimed in claim 3, wherein the point of intersection is situated on the separating line.

5. The method as claimed in claim 4, wherein the measurement of the absorption rate includes:

a third measurement of an absorption rate Am3 of the produced plasmonic antenna when it is exposed to a third incident radiation of wavelength $\lambda_m$ and with a direction of polarization parallel to the bisector of a first angular sector delineated by the first and second axes of alignment, a fourth measurement of an absorption rate Am4 of the produced plasmonic antenna when it is exposed to a fourth incident radiation of wavelength $\lambda_m$ and with a direction of polarization parallel to the bisector of a second angular sector delineated by the first and second axes of alignment, this second angular sector having a shared side with the first angular sector, and the determination of the magnitude of the misalignment includes determining the magnitude of the misalignment between the first and second zones, in a direction perpendicular to the separating line, depending on the difference between the ratio Tm3/Tm4 and a ratio Tp3/Tp4, where Tp3 and Tp4 are the predicted values of the absorption rate, in the absence of a misalignment, for the third and fourth measurements, respectively.

6. The method as claimed in claim 5, wherein, in the provided blueprint:

the orthogonal projections, in the plane of the substrate, of the first and fourth elements are symmetrical to the orthogonal projections, in the same plane, of the second and third elements about an axis perpendicular to the separating line, and the orthogonal projections of the first and third elements, in the plane of the substrate, are symmetrical to the orthogonal projections of the second and fourth elements about the separating line, and the orthogonal projection, in the plane of the substrate, of the first axis of alignment cuts the separating line at an angle of 45°.

7. The method as claimed in claim 1, wherein, in the provided blueprint, each element includes a tip whose apex is situated on one respective side of the cavity, each pair of elements whose apexes are facing one another and are situated on respective opposite sides of said cavity thus forming what is known under the name of a 'bowtie' antenna.

8. The method as claimed in claim 1, wherein the elements are made of an electrically conductive material.

9. The method as claimed in claim 1, wherein the elements are made of dielectric material and deposited directly on a layer made of electrically conductive material or correspond to cavities hollowed out of a layer made of dielectric material, which layer is deposited directly on a layer made of electrically conductive material.

10. The method as claimed in claim 1, wherein the wavelength $\lambda_m$ is less than 2000 nm or 700 nm.

11. The method as claimed in claim 1, wherein the first and second zones are:
- a first and a second field, respectively, situated in one and the same plane parallel to the plane of the substrate, of an electron beam lithography machine, or
- a first and a second structured layer, respectively, superimposed above one another.

12. An information recording medium wherein it includes instructions for implementing a measurement method as claimed in claim 1 when these instructions are executed by a microprocessor.

13. An apparatus for measuring the misalignment between a first and a second etching zone for implementing a measurement method as claimed in claim 1, this apparatus including:
- a source capable of emitting an incident polarized radiation of known intensity at a wavelength $\lambda_m$ over a plasmonic antenna produced on a substrate,
- a radiation intensity sensor capable of measuring the intensity of the radiation reflected by the plasmonic antenna or transmitted through the plasmonic antenna at the wavelength $\lambda_m$, and
- a microprocessor programmed to determine an absorption rate on the basis of the known intensity of the incident radiation and of the measured intensity of the reflected or transmitted radiation, wherein the microprocessor is programmed to determine the magnitude of the misalignment between the first and second zones on the basis of the measured absorption rate and of a predicted value of this absorption rate in the absence of a misalignment between the first and second zones.

14. A blueprint for a reference pattern for implementing a measurement method as claimed in claim 1, this blueprint containing instructions specific to an electron beam lithography machine that includes at least a first and a second separate field, said instructions encoding in particular the dimensions, the layout and the position, in the first and second fields, of at least one plasmonic antenna to be produced on a substrate, this plasmonic antenna being capable, after having been produced on the substrate, of producing surface plasmon resonance located inside a cavity when said antenna is exposed to polarized incident radiation of wavelength $\lambda_m$ such that the plasmonic antenna absorbs at least a portion of the polarized incident radiation at this wavelength $\lambda_m$, the absorption rate of this plasmonic antenna at the wavelength $\lambda_m$ varying depending on a dimension of the cavity, this plasmonic antenna including, to this end, a first and a second element that are separate and each delineate the cavity on one respective side such that the dimension of the cavity is set by the spacing between these first and second elements, these first and second elements each being situated entirely on a first and on a second respective side of a separating plane, respectively, wherein the encoded dimensions, layout and position of the plasmonic antenna are such that all of the elements of this plasmonic antenna that are situated on the first side of the separating plane are entirely inside the first field and all of the elements of the plasmonic antenna that are situated on the second side of the separating plane are entirely inside the second field.

* * * * *